United States Patent [19]

Theodoropulos

[11] Patent Number: 4,822,878

[45] Date of Patent: Apr. 18, 1989

[54] CYCLIC ANHYDRIDE DERIVATIVES OF CHROMOPHORS

[75] Inventor: Spyros Theodoropulos, Yorktown Heights, N.Y.

[73] Assignee: Viomedics, Inc., Worcester, Mass.

[21] Appl. No.: 197,344

[22] Filed: May 27, 1988

Related U.S. Application Data

[63] Continuation-in-part of Ser. No. 068,438, Jun. 30, 1987, abandoned.

[51] Int. Cl.$^4$ .................. C07D 265/28; C07D 237/32; C07D 311/82

[52] U.S. Cl. ...................................... 544/91; 260/377; 544/31; 544/37; 544/103; 544/227; 544/237; 546/107; 549/225; 549/232; 549/234; 549/237; 549/240; 549/244

[58] Field of Search .................. 260/377; 544/99, 103, 544/227, 237, 31, 37; 546/107; 549/225, 232, 234, 237, 240, 244

[56] References Cited

U.S. PATENT DOCUMENTS 4,600,775 7/1986 Theodoropulos .................... 544/99

Primary Examiner—Richard L. Raymond
Attorney, Agent, or Firm—Burgess, Ryan and Wayne

[57] ABSTRACT

Novel chromophor derivatives of cyclic anhydrides are provided which have the ability to react with a variety of organic substrates forming adducts which are useful in analytical techniques for the detection and measurement of biological compounds.

14 Claims, No Drawings

CYCLIC ANHYDRIDE DERIVATIVES OF CHROMOPHORS

This application is a continuation-in-part of application Ser. No. 068,438, filed June 30, 1987, now abandoned, the entire contents of which is hereby incorporated by reference.

FIELD OF THE INVENTION

This invention relates in general to novel anhydrides. In one aspect, this invention relates to anhydrides which are derivatives of chromophoric compounds which have the ability to react with a variety of organic substrates forming adducts which are useful in analytical techniques for the detection and measurement of biological compounds.

DESCRIPTION OF THE PRIOR ART

A variety of compounds have been reported in the literature as being useful in analytical techniques for the detection and measurement of biological properties and components of compounds of interest. Typcial components include, among other, bacteria, viruses, enzymes, drug and hormones. For example, it is known that fluorescent groups such as fluorescein isothiocyanate can be introduced into certain specific compounds of biological interest. However, analytical tehcniques employing conjugates of fluorescein isothiocyanate undergo bleaching of the conjugate when exposed to ultraviolet light resulting in rapid loss of fluorescence. Still further, isothiocyanate derivatization of chromophoric compounds is very limited and requires conditions for conjugation to organic substates to which not all substrates are stable.

Accordingly, one or more of the following objects can be achieved by the practice of this invention. It is an object of this invention to provide novel anhydrides of chromophors. Another object of this invention is to provide novel anhydride derivatives of chromophors which may be readily coupled to compounds of clinical interest. A further object of the present invention is to provide novel anhydrides which will exhibit distinct fluorescence excitation and emission spectra, corresponding to that of the specific class of chromophors. It is also an object of the present invention to provide anhydride derivatives of fluorescent molecules exhibiting superior stability over the native chromophors. A still further object of this invention is to provide processes for the conjugation of the novel chromophoric derivatives to organic substrates in conditions to which the organic substrates exhibit higher stability. Another object of this invention is to provide processes for the preparation of the novel chromophoric derivatives. A still further object of this invention is to provide processes for the use of the derivatives for the detection and measurement of biological compounds. These and others will readily become apparent to those skilled in the art in the light of the teachings herein set forth.

SUMMARY OF THE INVENTION

In this broad aspect, the present invention is directed to novel anhydride derivatives of chromophoric compounds, processes for their preparation and use in the measurement and detection of biological compounds.

DETAILED DESCRIPTION OF THE INVENTION

The present invention is directed to novel cyclic anhydride derivatives of chromophoric compounds. The cyclic anhydride moiety allow the coupling of these chromophors to a variety of biological molecules of clinical interest. The basic structure of the anhydride derivatives of chromphors which are prepared by the teachings of this invention are conveniently represented by the structural formula:

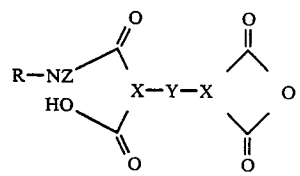

wherein R is an organic radical exhibiting chromophoric characteristics such as fluorescence, luminescence, chemiluminescence or absorption of analytical value. Z is hydrogen, alkyl, aryl, or a heterocyclic group composed of carbon, hydrogen and at least one of oxygen, nitrogen or sulfur, and wherein Z contains from 1 to 20 carbon atoms; each X contains 2 to 3 straight chain carbon atoms connecting the carbonyl groups; and Y is a divalent or polyvalent group comprised of carbon, hydrogen and optionally oxygen, and wherein Y contains up to 20, preferably 2 to 12, carbon atoms, and provides at least one single or multivalent alkyl, alkylenyl, cycloalkyl, bicycloalkyl, bicycloalkenyl, aryl, or carbonyl containing group bridging the carbonyl-containing moieties through one or more of the carbon atoms of the X groups. Preferably, Y is a hydrocarbon group which may contain a carbonyl group. Typical examples of cyclic anhydride derivatives of chromophors are as follows:

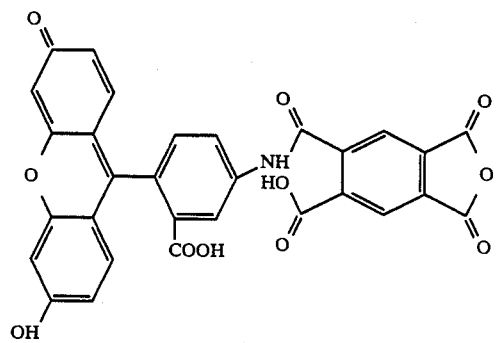

Benzophenone-3'-(N—5-fluoresceinyl-amino-carbonyl)-

4'-carboxylic-3,4-dicarboxylic acid-anhydride.

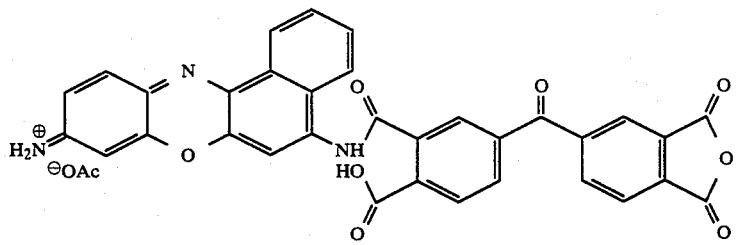

Benzophenone-3'-(cresyl violet-carbonyl)-4'-carboxylic-3,4-dicarboxylic acid-anhydride.

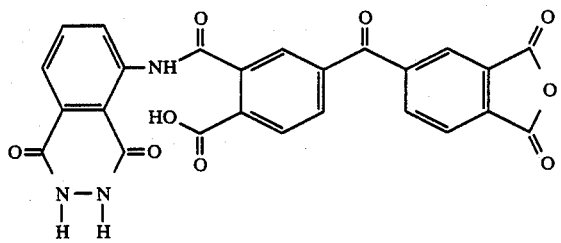

Benzophenone-3'-(luminol-carbonyl)-4'-carboxylic-3,4-dicarboxylic acid-anhydride.

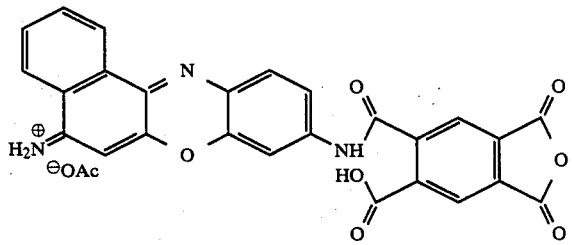

Cresyl Violet-phthalic Anhydride

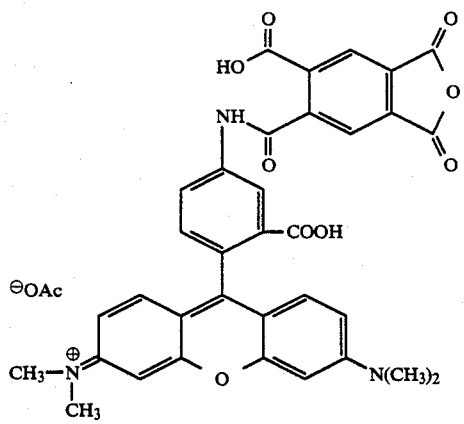

Tetramethylrhodamine-phthalic Anhydride

The anhydride derivatives of chromophors are conveniently synthesized using known techniques. In practice, a chromophor having an active amine group is allowed to react with a cyclic dianhydride to afford the anhydride derivative of the chromophor. The process of the present invention can be illustrated by the synthesis of cresyl violet-anhydride as shown in the following equation:

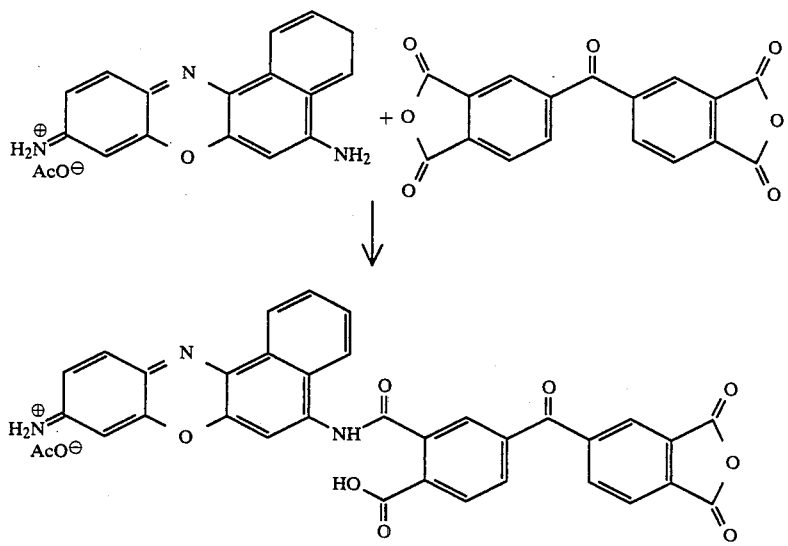

In general a variety of cyclic dianhydrides when in excess, would react with chromophors having an active amino group to form derivatives of the chromophors of cyclic dianhydrides among others are shown below:

-continued

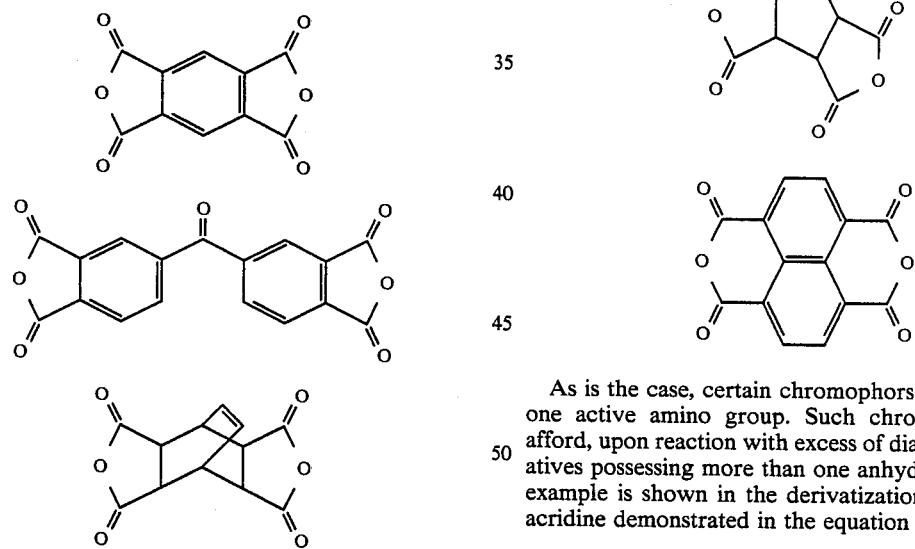

As is the case, certain chromophors have more than one active amino group. Such chromophors would afford, upon reaction with excess of dianhydride, derivatives possessing more than one anhydride moiety. An example is shown in the derivatization of 3,9-diamino acridine demonstrated in the equation below:

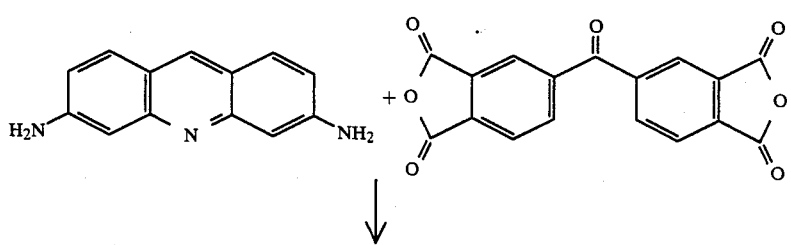

-continued

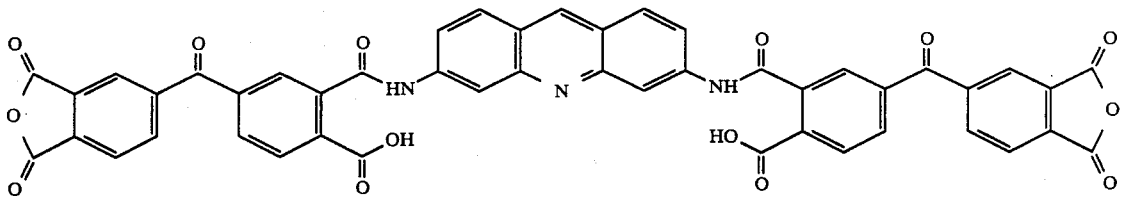

The reaction of the chromophors with cyclic dianhydrides is optionally performed in the presence of a solvent which is inert to the reactants and reaction products. Suitable solvents which can be employed include, among others, aliphatic or aromatic chlorinated hydrocarbons, ethers, esters, pyridine, acetic acid, amides and the like. Particularly preferred for use as the solvent is acetic acid.

The process can be conducted at temperatures from about −10 to about 150° C. with ambient temperatures being preferred.

In another aspect of this invention, the anhydride of the general formula I can react with an organic substrate containing a functional group having an active hydrogen. For example, conjugates of the chromophors of this invention and organic substrates can be conveniently represented by the formula:

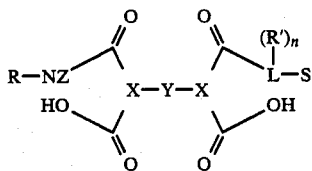

II

Wherein R is a chromophor exhibiting fluorescence, luminescene, chemiluminesence or absorption of analytical value; S is an organic substrate containing a functional group having an active hydrogen as hereinafter defined; L is nitrogen or oxygen; R' is hydrogen, alkyl, aryl or heterocycyl having from 1 to 20 carbon atoms; n is 0 or 1, with the proviso that when L is oxygen, n is 0; X, Y and Z have the same values as previously indicated.

Thus, the compounds of the present invention can be conveniently coupled to an inert matrix or organic substrate by known techniques to provide novel conjugates or adducts as indicated above. The compounds can be coupled either directly or indirectly to the inert matrix in organic substrate, preferably a biological material, and hence render such compounds useful in a variety of qualitative and quantitive determinations of one or more immunochemically reactive components in biological systems. Therefore, the chromophoric compounds can be coupled to a wide variety of biologically acceptable substrates which are normally employed in the detection and measurement of biological compounds. The only requirement of the matrix or substrate is that it contain one or more active sites through which coupling with the chromophoric derivative can be effected. In practice, such sites usually contain an active hydrogen and include, but are not limited to, primary amines, secondary amines, hydroxyls groups mercapto groups and the like. As indicated, coupling of the chromophoric derivatives to the matrix or substrate is effected by methods known to those skilled in the art to which this invention pertains.

It is therefore possible to form conjugates of the chromophoric derivatives with a wide variety of organic substrates, including, drugs, antigens, antibodies, haptens, peptides, proteins, amino acids, gamma globulin, avidin, bovine serum albumen, conalbumen, enzymes, and the like. A particularly preferred inert substrate which is widely used in the detection and measurement of biological compounds is the spherical beads or particles employed in chromatographic analytical techniques. For example, the derivatives of this ivention can be conveniently coated on, or sensitized to, small beads or particles such as those composed of polystyrene or other inert biological compositions.

The chromophoric derivatives of the present invention are therefore useful in a wide variety of areas as a biochemical tool for the detection and measurement of biological compounds, particularly, immunochemically reactive components, such as those found in body fluids, cells and cell components. For example, the derivatives can be employed as conjugates with an inert matrix or organic substrate for use in antigen-antibody assays. Molecules, such as fluorescein or rhodamine are currently employed for fluorescence microscopy in indirect immunocytochemistry. Due to their improved stability, resistance to bleaching and the wide spread between excitation and emission, the derivatives of the present invention are ideally suited for replacement of the fluorescein currently employed in fluorescent antibody determinations.

The present invention is also directed to an immunoassay wherein an immunochemically active compound is coupled directly or indirectly to the novel chromophoric derivatives of the present invention, whereby during or after a set period of time for the immunochemical reaction to occur, and possibly after separtion of the free and bound labelled components, the quantity of the chromophoric compound is determined in the test medium, or a separated fraction thereof, and wherein the determination provides a qualitative and-/or quantitive indication of the immunochemical reactive component to be determined.

Accordingly, one aspect of the present invention relates to a particularly attractive procedure for the qualitative and/or quantitative determination of an immunochemically reactive component, including antibodies, antigen, haptens, and the like in test media including animal or human body fluids, such as blood serum, urine, and the like, and animal and human cells and components thereof.

The invention therefore also includes novel immunochemical reagents, composed of the aforementioned derivatives which may be in the form of dispersions, or polymeric nuclei coated with the chromophoric derivative, to which an immunochemically reactive component has been attached directly or indirectly. Also included within the scope of the invention are test kits containing the aforesaid immunochemical reagent.

In practice, the immunochemically reactive component labelled with the chromophoric derivatives of the present invention are employed in "test kits" as reagents in combination with other known reagents for the qualitative and/or quantitative determination of components suchs as haptens, antigens, antibodies and the like, using known assay methods. For example conventional immunochemical test procedures such as competitive immunoassay, sandwich techniques, and those test based on the agglutination principle can utilize the derivatives of the present invention.

For instance, in a conventional competitive immunoassay, a test sample containing an unknown quantity of antigen is brought into contact with a certain quantity of the corresponding antigen labelled with a chromophoric compound and an antibody attached to an insoluble carrier which is directed against this antigen, or a certain quantity of antigen attached to an isobule carrier and an anitbody labelled with the chromophor directed against this antigen. Upon completion of the reaction, the quantity of the chromophor is determined in the free or bound fraction which provides an indication of the antigen to be determined.

The derivatives of the present invention are accordingly useful for the determination of a wide variety of immunochemical components of body fluids and cells and includes, but not limited to human chorionic gonadotropin (HCG), hepatitis Surface B antigen (HBsAg), human placental lactogen (HPL), human anti-Rubella sera, human prolactin (PRL), testosterone, human T-cell leukemia virus (HTLV), adult T-cell leukemia associated antigen producing cells, and the like. The derivatives of the present invention are also useful in conjunction with SDS gel electrophoresis for the study of peptide fragments from the cleavage of proteins. In such studies, chromatography and electrophoresis provide a 2-dimensional map or "fingerprint" diagnosis of a protein.

The derivatives of the present invention are also useful as a replacement for radioactive tracers in automated electrophoresis processes such as those employed in determining the sequence of nucleid acids in genes. Newly available analytical instruments, such as the DNA sequencer developed at the California Institute of Technology are currently in use to expedite gene mapping of strands of DNA. In the current version of these instruments a laser and fluorescent dyes replace the use of radioactive materials and result in markedly increased savings in the time needed to effect the mapping. In the DNA sequencer amino acids exposed to intense light cause the dye to glow. By computer analysis of the intensity of color, the identity of the nucleic acid base can be determined. The chromophoric derivatives of the present invention are particularly attractive for this application due to their stability in the present of high intensity light such as lasers empolyed in the DNA sequencer, and the distinct wide spread between the points of excitation and emission. Additionally, as previously indicated, the derivatives of the present invention are resistant to bleaching and hence are ideally suited for this application.

As previoualy indicated, the anhydride derivatives of this invention are bifunctional. The amide moieties of the chromophors are ideal labeling agents due to their photochemical stability and the distinct characteristics exhibited by the same. Cresyl violetanhydride of the present invention, for example, shows an excitation at 470nm and an emission at 580nm, while the native chromophor exhibits an excitation at 590nm and an emission at 625nm. Fluorescein of fluorescein-isothiocyanate, a readily available chromophor, has been found to undergo rapid bleaching or loss of fluorescence when exposed to ultraviolet light. In contrast, the anhydride derivative of the inveniton exhibit superior stability to ultraviolet light and undergo little or no bleaching. The anhydride moiety of the chromophors of the present invention is a very reactive groups and permits conjugation of the chromophors to substrates in a wide range of pH, being either basic or acidic. The isothiocyanato moiety in contrast allows coupling of chromophors only at the pH levels of 8 or above, thus eliminating coupling to substrates which are not stable in acidic pH. The anhydride derivatives of the chromophors of the present invention are thus particularly useful in labeling biological compounds. It has also been observed that the compounds of the invention are also useful as staining materials for the staining or cells and as indicators.

The unique chromophors can also be incorporated in spherical polystyrene beads or other spherical polymeric beads for use as standards for fluorescence assays. They are also useful as fluorescence standards for alignment of fluorescence activated flow cytometers. Additionally, the chromophors are also useful to develop non-radiometric fluorescence detection of DNA-DNA and DNA-RNA hybridization.

The following examples illustrate the best mode presently contemplated for the practice of this invention.

EXAMPLE 1

Benzophenone-3'-(Cresyl violet-carbonyl)-4'-carboxylic-3,4-dicarboxylic acid-anhydride A mixture of 321 milligrams (0.001 mol) of cresylviolet acetate and 966 milligrams (0.003 mol) (excess) of 3,3'-4,4'-benzophenone-tetracarboxylic acid dianhydride was dissolved in 15 milliliter of glacial acetic acid and allowed to stir at ambient temperature for about 17 hours. The acetic acid was then removed in vacuo and the product was washed with acetone. 600 milligrams of cresylviolet anhydride were obtained. Ultra-violet absorption in ethanol showed maxima at 500nm; 1R(nujol) analysis showed bands at 5.62(anhydride),5.8-5(amide)6.0(carboxylic), 6.33, 6.85, 7.48, 7.68, 7.94, 8.13, 8.62, 8.85, and 9.03$\mu$

EXAMPLE 2

3'-Nilebluecarbonyl-4'-carboxylic-benzophenone-3,4-dicarboxylic acid anhydride

A mixture of 200 milligrams of nile blue hydrochloride and 600 mg of 3,3'-4,4'-benzophenone-tetracarboxylic acid dianhydride was dissolved in 5ml of glacial acetic acid and allowed to stir at ambient temperature for 3 days. The solvent was removed in vacuo and the product was washed with acetone. 200 milligrams of nile blue anhydride were obtained. Infrared (nujol) analysis showed bands at 5.40; 5.62(anhydride); 5.95(amide); 6.3, 6.45, 6.85, 7.05, 7.25, 7.40, 7.50$\mu$

EXAMPLE 3

3'-fluoresceinaminocarbonyl-4'-carboxylic-benzophenone-3,4-dicarboxylic acid dianhydride A mixture of 250 milligrams of 5-aminofluorescein and 483 milligrams of 3,3'4,4'-benzophenone-tetracarboxylic acid dianhydride was dissolved in 30 milliliters of dioxane and allowed to stir at ambient temperature for 3 hours. The solvent was then removed in vacuo and the product was washed with 30 percent acetone-methylenechloride. 280 milligrams of fluorescein-anyhdride were obtained. infrared (nujol) analysis showed bands at 1850, 1775(anhydride), 1725 (amid), 1665(carboxylic), 1600, 1570 cm$^{-1}$.

EXAMPLE 4

2-Cresylvioletcarbonyl-3-carboxylic-bicyclo[2.2.2]oct-7-ene-5,6-dicarboxylic acid anhydride A mixture of 321 milligrams of cresylviolet acetate and 1.0 gram of bicyclo[2.2.2]oct-7-ene-2,3,5,6-tetracarboxylic-2,3,5,6-dianhydride were dissolved in 10 milliliters of dioxane and allowed to stir at ambient temperature for 5 days. The product was filtered off and washed once with dioxane and twice with acetone. 380 milligrams of cresyl violet-anhydride were obtained. Ultraviolet absorption (methanol) showed maxima at 590nm. Infrared absorption (nujol) showed bands at 1845 and 1770(anhydride), 1700, 1640, 1585, 1540, 1515, 1330, 1300, 1230, 1095, 1055, 1000, 930.

EXAMPLE 5

Coupling of fluorescein-anhydride to protein

3'-fluoresceinyl-amino0-carbonyl-4'-carboxylic-3,4'-dicarboxylic acid dianhydride (simply referred to as fluorescein anhydride) 10 milligrams (0.015 mmol), was directly added to a protein solution containing 10 milligrams (0.00013mmol) of albumin in a 2 ml aliquot of 0.1M phophate buffer, PH 7.0 and stirred at ambient temperature for 4 hours. The mixture was then filtered through a membrane filter (nuclipore 3$\mu$m) and purified on a 1.5x10 cm sephadex G50 column using same buffer. The conjugate fraction was then passed through a sephadex PD-10 column to remove the salts and lyophilized.

EXAMPLE 6

5-Cresylviolet Carbonyl-4-carboxylic-1,2-benzene-Dicarboxylic Acid Anhydride 321 milligrams of cresylviolet acetate and 660 milligrams of 1,2,4,5-benzenetetracarboxylic acid anhydride were mixed in 20 milliliters of acetic acid and allowed to stir at ambient temperature for 24 hours. The solvent was then removed in vacuo and the product was washed with acetone. 480 milligrams of the product obtained. Infrared analysis (nujol) showed bands at 1840 and 1785 (anhydride), 1650, 1580, 1525, 1305, 1250, 1100, 1050, 1000, 880, 855, 830 and 720 cm 1.

EXAMPLE 7

Preparation of 5-Tetramethylrhodamine Amino Carbonyl-4-carboxylic-1,2-benzene Dicarboxylic Acid Anhydride (Tetramethylrhodaminebenzene-anhydride 200 milligrams of tetrtamethylrhodamine amine and 600 mg of 1,2,4,5-benzenetetracarboxylic acid diahydride were mixed in 30 milliliters of glacial acetic acid and the mixture was stirred at about 50° C. for 15 hours. The solvent was removed in vacuo and the product washed with acetone. 180 milligrams of the product were obtained. Infrared analysis (nujol) showed bands at 1845 and 1775 (anhydride), 1720, 1590, 1340, 1250, 1220, 1185, 1120, 825, 820, 785, and 720 cm 1.

EXAMPLE 8

Labeling of Polystyrene Beads with 5-Cresylviolet-4-carboxylic-1,2-benzene Dicarboxylic Acid Anhydride Polystyrene beads having a diameter of 10 microns were precipitated by centrifugation and the supernatent was removed by decantation. The beads were washed twice with methanol and dried by passing a stream of air. The beads were suspended in chloroform. To the chloroform suspension was added a drop of a dimethylsulfoxide solution and cresylviolet-benzene-anhydride and the mixture kept at ambient temperature for 15 hours. The chloroform was removed by passing a stream of air and the beads washed with methanol to remove excess of cresylviolet-benzene-anhydride. The beads were resuspended in 1 percent sodium dodecylsulfate in distilled water for further use.

EXAMPLE 9

Coupling of Cresyl Violet-benzene-anhydride to Streptavidin 0.7 milliliters containing $5\times10^{-7}$ mol of the anhydride of example 6 in DMSO was added to 1 milligram streptavidin ($1.7\times10^{-8}$ mol) dissolved in 0.4 milliliter of phosphate buffer. The solution was stirred gently at room temperature for 2–4 hours in a small brown vial. It was then centrifuged in a Beckman microcentrifuge for 5 minutes. Protein conjugate was separated from free dye on a 1×25 cm Sephadex G50 column with the same buffer. Protein-containing fractions were pooled and concentrated by centrifugation across a 30,000 MW cut-off membrane (Amicon "Centricon-30"). Protein concentration and dye:protein ratio were determined by absorption spectroscopy. The protein conjugate was stored in a brown vial at 4' C. with 0.02 percent sodium azide.

EXAMPLE 10

Coupling Fluorescent Dyes to Proteins Fluorescein Anhydride-Gamma Globulin 0.15 milliliters containing $1.88\times10^{-7}$ mol fluorescein anhydride in 0.1 M phosphate buffer, pH 7.5, was added to 1 mg human gamma globulin ($6\times10^{-9}$ol) dissolved in 0.4 ml phosphate buffer. The solution was stirred gently at room temperature for 2–4 hours in a small brown vial. It was then cnetrifuged in a Beckman microcentrifuge for 5 minutes. Protein conjugate was separated from free dye on a 1×25 cm Sephadex G50 column with the same buffer. Protein-containing fractions were pooled and concentrated by centrifugation across a 30,000 MW cut-off membrane (Amicon "Centricon-30"). Protein concentration and dye:protein ratio were determined by absorption spectroscopy. The protein conjugate was stored in a brown vial a 4° C. with 0.02 percent sodium azide.

EXAMPLE 11

Staining Mammalian Cells with Fluorescent Antibodies Against Cell-Surface Antigens Rat T-lymphocytes were teased out of 4–6 cervical lymph nodes and washed once by centrifugation at 1000 ×g in ice-cold balanced salt solution (BSS) with 0.5 percent fetal bovine serum (FBS). BSS contained 5.55 mM dextrose, 0.041 mM KH$_2$PO$_4$, 1.33 mM Na$_2$HPO$_4$, 1.27 mM CaCl$_2$, 5.36 mM KCl, 137 mM NaCl, 0.98 mM MgCl$_2$ and 0.81 mM MgSO$_4$, pH 7.2. 1×10−6 cells were incubated with 25 ul appropriately diluted biotinylated OX19 (mouse monclonal antibody against rat T cells) in 12×75 mm polystyrene tubes for 30 minutes on ice. Cells were washed in 2 milliliters BSS/FBS and then incubated for 30 minutes with 25ul appropriately diluted fluorescein anhydride-conjugated streptavidin. Cells were washed in 2 ml BSS/FBS and resuspended in 0.05 ml BSS/FBS for immediate examination by fluorescence microscopy. Remaining cells were then fixed by a 5 minute incubation at room temperature with 0.5 percent paraformaldehyde in BSS, washed in 2 ml BSS/FBS, and stored at 4° C. in BSS/FBS for subsequent flow cytometric analysis.

Although the invention has been illustrated by the proceeding examples, it is not to be construed as being limited to the materials employed therein, but rather, the invention is directed to the generic area as hereinbefore disclosed. Various modifications thereof can be made without departing from the spirit or scope thereof.

What is claimed is:

1. Cyclic anhydride derivatives of chromophors having the structural formula:

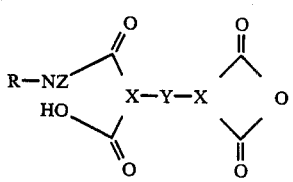

wherein R is an organic chromophoric group exhibiting fluorescence, luminesence, chemiluminescence or absorption properties; Z is hydrogen, alkyl, aryl, or a heterocyclic group composed of carbon, hydrogen and at least one of oxygen, nitrogen or sulfur, and wherein Z contains from 1 to 20 carbon atoms; each X contains 2 to 3 straight chaing carbon atoms connecting the carbonyl groups; and Y is a divalent or polyvalent group comprised of carbon, hydrogen, and optionally oxygen, and contains up to 20 cargon atoms, and provides at least one single or multivalent alkyl, alkenyl, cycloalkyl, bicycloalkyl, bicycloalkenyl, aryl or carbonyl containing group bridging the carbonyl-containing moieties through one or more of the carbon atoms of the X groups.

2. The anhydride derivative of chromophors of claim 1 having the structural formula:

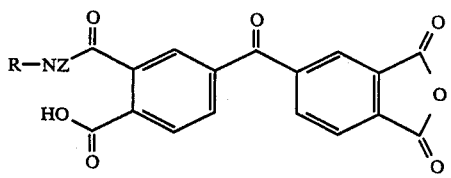

wherein R and Z are as indicated.

3. The anhydride derivative of claim 2 wherein R is is selected from the group consisting of fluorescein, rhodamine, cresyl violet, Nile blue A, an oxazine, a thiazine and luminol.

4. The anhydride derivative of chromophors of claim 1 having the structural formula:

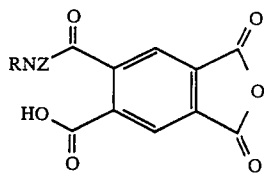

wherein R and Z are as indicated.

5. The anhydride derivative of claim 4 wherein R is selected from the group consisting of fluorescein, rhodamine, cresyl violet, Nile blue A, an oxazine, a thiazine and luminol.

6. The anhydride derivative of chromophors of claim 1 having the structural formula:

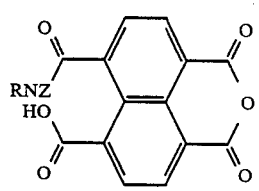

wherein R and Z are as indicated.

7. The anhydride derivative of chromophors of claim 1 having the strucutural formula:

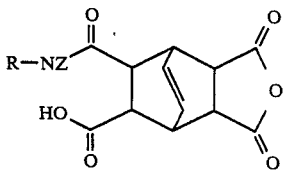

wherein R and Z are as indicated.

8. The anhydride derivative of chromophors of claim 1 having the structural formula:

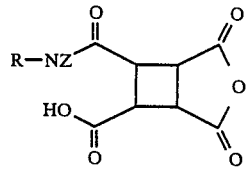

wherein R and Z are as indicated.

9. The anhydride derivative of chromophors of claim 1 having the structural formula:

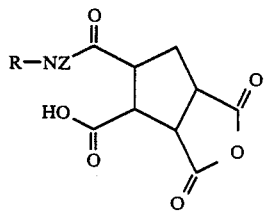

wherein R and Z are as indicated.

10. The anhydride derivative of chromophors of claim 1 having the structural formula:

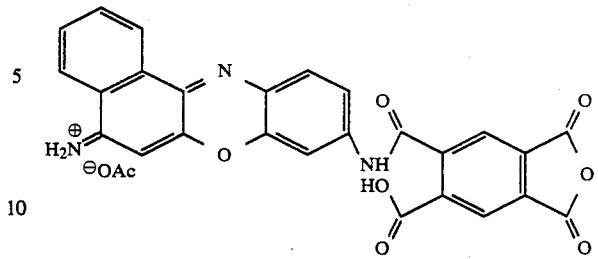

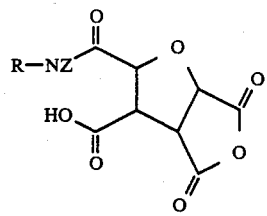

wherein R and Z are as indicated.

11. The anhydride derivative of chromophors of claim 1 having the structural formula:

13. The anhydride derivative of chromophor of claim 1 having the structural formula:

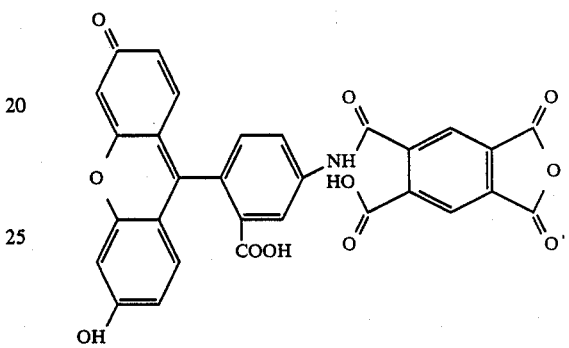

14. The anhydride derivative of chromophors of claim 1 having the structural formula:

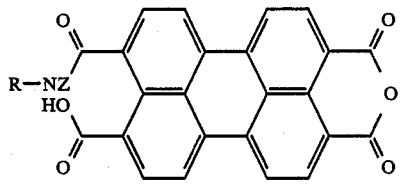

wherein R and Z are as indicated.

12. The anhydride derivative of chromophor of claim 1 having the structural formula:

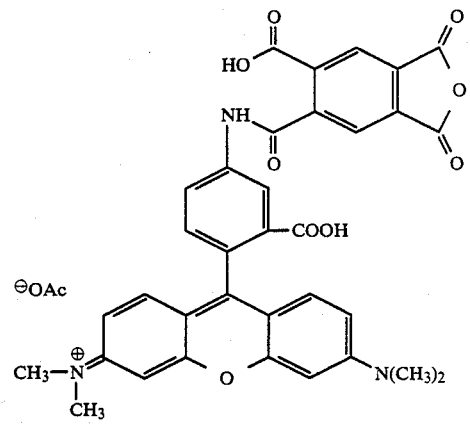

* * * * *